(12) United States Patent
Tchirikov et al.

(10) Patent No.: US 9,839,767 B2
(45) Date of Patent: Dec. 12, 2017

(54) CATHETER

(71) Applicants:"National Laboratory Astana" Private Institution, Astana (KZ); Michael Tchirikov, Halle (DE)

(72) Inventors: Michael Tchirikov, Halle (DE); Sharman Almaz, Astana (KZ); Znaxybay Sh. Zhumadilov, Astana (KZ); Gauri Bapayeva, Astana (KZ)

(73) Assignee: "National Laboratory Astana" Private Institution, Astana (KZ)

( * ) Notice: Subject to any disclaimer, the term of this patent is extended or adjusted under 35 U.S.C. 154(b) by 754 days.

(21) Appl. No.: 13/742,420

(22) Filed: Jan. 16, 2013

(65) Prior Publication Data
US 2013/0184647 A1    Jul. 18, 2013

(30) Foreign Application Priority Data

Jan. 16, 2012  (EP) ..................................... 12151259

(51) Int. Cl.
| | | |
|---|---|---|
| *A61M 25/02* | (2006.01) | |
| *A61M 25/04* | (2006.01) | |
| *A61M 25/00* | (2006.01) | |

(52) U.S. Cl.
CPC ............ *A61M 25/02* (2013.01); *A61M 25/04* (2013.01); *A61M 25/0017* (2013.01); *A61M 2025/028* (2013.01); *A61M 2025/0213* (2013.01); *A61M 2025/0286* (2013.01)

(58) Field of Classification Search
CPC .......... A61M 25/02; A61M 2025/0213; A61M 2025/028; A61M 2025/0286; A61M 2025/0293; A61M 25/04; A61M 37/0069; A61F 2/95; A61F 2002/9505
See application file for complete search history.

(56) References Cited

U.S. PATENT DOCUMENTS

| | | | |
|---|---|---|---|
| 3,397,699 A | | 8/1968 | Kohl |
| 3,996,938 A | | 12/1976 | Clark, III |
| 4,474,569 A | | 10/1984 | Newkirk |
| 4,699,611 A | * | 10/1987 | Bowden .................... A61F 2/04  604/105 |
| 4,986,810 A | * | 1/1991 | Semrad ................. A61M 25/04  604/106 |
| 4,987,079 A | | 1/1991 | Cullor |
| 5,112,310 A | * | 5/1992 | Grobe .......................... 604/175 |
| 5,278,564 A | | 1/1994 | Groenenboom |
| 5,279,564 A | * | 1/1994 | Taylor ........................... 604/104 |
| 5,282,860 A | | 2/1994 | Matsuno et al. |
| 6,629,987 B1 | * | 10/2003 | Gambale et al. ............. 606/198 |

(Continued)

FOREIGN PATENT DOCUMENTS

SU    1764660    9/1992

OTHER PUBLICATIONS

Search Report dated Jul. 16, 2013 From the Eurasian Patent Organization, The Eurasian Patent Office Re. Application No. 201300020.

*Primary Examiner* — Quynh-Nhu H Vu
*Assistant Examiner* — Nilay Shah

(57) ABSTRACT

The present invention relates to a catheter for realizing a volume flow into or out of a human or animal organ, comprising a catheter tube and, at a distance from the distal end of the catheter, an affixing device for mechanically affixing the catheter in the tissue of a human or animal organ.

20 Claims, 2 Drawing Sheets

(56) References Cited

U.S. PATENT DOCUMENTS

2004/0122456 A1\* 6/2004 Saadat ............. A61B 17/00234
606/157
2005/0187578 A1 8/2005 Rosenberg et al.
2006/0229553 A1\* 10/2006 Hammack et al. ........ 604/96.01
2007/0156117 A1\* 7/2007 Adams ................ A61J 15/0015
604/533

\* cited by examiner

CATHETER

RELATED APPLICATION

This application claims the benefit of priority of European Patent Application No. 12151259.4 filed on Jan. 16, 2012, the contents of which are incorporated herein by reference in their entirety.

FIELD AND BACKGROUND OF THE INVENTION

The present invention relates to a catheter for realising a volume flow into or out of a human or animal organ.

An Intrauterine Growth Restriction (IUGR) of the foetus occurs among 3 to 5% of all pregnancies in cases of placenta insufficiency and presents a serious complication during the pregnancy. The growth retardation significantly increases the risk of premature birth, and is responsible for the poor neonatal outcome or even death of the child.

The death rate in cases of IUGR is increased by the 3 to 10-fold. Around 25 to 40% of all intrauterine foetal deaths are caused by IUGR.

The intrauterine growth retardation is also regarded as being the cause of the development of metabolic syndrome, as well as of an increased risk of developing coronary heart diseases, heart attacks and diabetes mellitus type 2.

In case of IUGR, the transportation of amino acids through the placenta is significantly reduced.

There is no proven causal method for treating placenta insufficiency since an "insufficient" placenta develops during early pregnancy, with the subsequent foetal growth retardation occurring at the end of the 2nd trimester.

Conventional catheters are not optimally designed for supplying nutrients since nutrients must be supplied over relatively long periods of time, and consequently there is a risk that the catheter may be displaced by movements of the foetus and/or of the mother.

SUMMARY OF THE INVENTION

The object of the invention is therefore to ensure the transportation of nutrients, such as amino acids and glucose, in a flexible, reliable and compatible manner, thus prolonging the pregnancy.

In order to attain this object, according to the invention, a catheter is provided to realise a volume flow into or out of a human or animal organ, which comprises a catheter tube and, at a distance from the distal end of the catheter, an affixing device for mechanically affixing the catheter in the tissue of a human or animal organ. The affixing device is in particular designed for the purpose of affixing the catheter tube in a placenta or in the cavum uteri of the uterus (amnion) in order to ensure a positioning of the distal end of the catheter tube e.g. in the umbilical vein (vena umbilicalis) of a foetus.

Preferably, the catheter is designed in such a manner that the affixing device abandons its affixing effect when a specific tensile force of 20 N acts on the catheter tube. This means that the catheter is designed in such a manner that even a slight tensile force in the direction of the proximal end is sufficient to be able to withdraw the catheter tube from the tissue. Here, the specific tensile force is selected in such a manner that, in relation to the surface on which on average the affixing elements of the affixing device act on the tissue, the tensile strength of the tissue is sufficiently high that, when the specific tensile force comes into effect, the affixing device abandons its affixing effect before the tissue is damaged. Meanwhile, the affixing device remains in the tissue.

In particular, it can be provided that the affixing device abandons its affixing effect when a tensile force of 10 N acts on the catheter tube. Preferably, the affixing effect should already be abandoned from a tensile force from 5 N to 10 N, in particular when anchored in the placenta. This means that, depending on the respective purpose of use, e.g. infusion into the vena umbilicalis and the affixing of the catheter in the placenta, a lower tensile force such as e.g. 5 or 10 N should be sufficient to abandon the affixing effect. When using the catheter for amnioinfusion following a premature breaking of the waters and an affixing of the catheter tube to the uterus wall, the affixing device should only abandon its affixing effect with a tensile force of approx. 20 N, or with a tensile force of 30 N and above. When using the catheter according to the invention in an advanced stage of pregnancy, the catheter can also be designed in such a manner that it abandons the affixing effect with a tensile force of 40 N or even 50 N and above, in particular when anchored in the uterus and with a corresponding structural design.

Advantageously, the affixing device should here be arranged at a distance of one-tenth to one-third of the length of the catheter from the distal end of the catheter.

Here, the affixing device can be designed as a stent which comprises a hollow cylinder section made of mesh material. This hollow cylinder section can, if necessary, be provided on one and/or both sides with a hollow truncated cone or a hollow spherical segment, wherein the hollow truncated cone or hollow spherical segment is preferably made of the same mesh material as the hollow cylinder section.

In this embodiment in particular, the catheter according to the invention is advantageously designed if the stent expands, due to its elasticity, when tensile stress acting in the longitudinal axis of the hollow cylinder is reduced. The reduction of tensile stress acting on the hollow cylinder occurs e.g. when a mandarin is withdrawn from the catheter tube, as a result of which a tensile stress which had previously acted on the catheter tube through the mandarin is removed. Here, the stent expands due to its elasticity, so that its diameter is enlarged and it can attach itself in a force and/or form-fit manner to the wall of an opening in the tissue, thus creating a relatively fixed mechanical connection between the tissue and the catheter tube.

In addition, or in an alternative embodiment of the stent, this can be designed in such a manner that it expands when heat is applied. This means that, when its temperature is increased, it changes its form in such a manner that its diameter is enlarged, so that it can attach itself in a force and/or form-fit manner to the wall of an opening in the tissue, thus creating a relatively fixed connection between the tissue and the catheter tube. This property of the stent can be realised e.g. through a suitable form memory alloy as mesh material.

In a further, alternative embodiment, it is provided that the affixing device is a brace element which, in profile, is in comparison further away from the longitudinal axis of the catheter tube than the outer side of the catheter tube. The profile in question here refers to the profile running transverse to the longitudinal axis of the catheter tube. Due to this design of the affixing device as a brace element, a type of barb is created which enables mechanical affixing of the catheter tube in the tissue of the organ.

Here, it can in particular be provided that the brace element is elastic, and the catheter tube essentially runs tangentially to the brace element. In a particularly preferred embodiment, the catheter tube runs precisely tangentially to the brace element. The elasticity module of the brace element should here be from 0.01 to 0.3 kN/mm². The brace element can be a diagonally cut pipe segment which is pushed onto the catheter tube, or it can be an integral section of the catheter tube.

In an alternative design, it is provided that the catheter has a force, form and/or material-fit connection between the affixing device and the catheter tube, and this force, form and/or material-fit connection is designed in such a manner that it is released when the specific tensile force acts on the catheter tube. Here, the connection between the catheter tube and the affixing device can be embodied by an integral design of the catheter tube, so that the catheter tube material forms a protrusion or projection as a brace element. In this case, the material section which connects the affixing device with the catheter tube is designed in such a manner that it shears off, rips or bends when the specific or a greater tensile force acts on the catheter tube, so that no affixing effect is sustained.

In an alternative embodiment, the affixing device is connected to the catheter tube by means of an adhesive connection, i.e. in a material-fit manner, or is connected to the catheter tube like a collar in a force and/or form-fit manner.

In these designs, the adhesive connection or the sleeve with its radial tension and/or form-fit holding force is designed in such a manner that it is released when the specific or a greater tensile force acts on the catheter tube. Here, a combination of the embodiments with the adhesive connection and the sleeve is also possible.

A further alternative design is that the catheter comprises a distal form element over or on the catheter tube in relation to the position of the affixing device, the largest dimension of which in profile is larger than the profile of the catheter tube, wherein the catheter comprises a force, form and/or material-fit connection between the form element and the catheter tube, and said force, form and/or material-fit connection is designed in such a manner that it is released when the specific tensile force acts on the catheter tube. The largest dimension of the form element is thus also larger than the clear width of the opening in the affixing device through which the catheter tube is guided. During normal use, the form element prevents a displacement of the affixing device in relation to the catheter tube. However, when the specific tensile force is applied to the proximal end of the catheter tube, the connection between the form element and the catheter tube is released, enabling the catheter tube to be withdrawn from the tissue and the affixing device to remain in the tissue. Said form element here acts as a type of blocking element for blocking a relative movement between the affixing device and the catheter tube during normal use of the catheter. Here, the form element does not necessarily have to be firmly connected to the affixing device.

Here, the form element can also be connected by means of an adhesive connection, i.e. in a material-fit manner, with the catheter tube, or be connected in a force and/or form-fit manner with the catheter tube. In these designs, the adhesive connection or the radial tension and/or form-fit holding force is designed in such a manner that it is released when the specific or a greater tensile force acts on the catheter tube.

In a further alternative design, the catheter comprises a distal form element over or on the catheter tube in relation to the position of the affixing device, the largest dimension of which in profile is larger than the profile of the catheter tube, wherein the affixing device is designed in such a manner that, due to the specific tensile force acting on the catheter tube, it expands on its edge facing towards the catheter tube and the form element in such a manner that the catheter tube can be drawn together with the form element through the affixing device. Here, the form element moves from the distal side of the affixing device to the proximal side of the affixing device. This design is particularly suitable if the affixing device comprises the hollow cylinder section created from mesh material, on which, on at least the side of the form element, a hollow truncated cone or a hollow spherical segment is arranged. These only expand so far that the form element can be drawn through the affixing device when the specific tensile force is applied to the catheter tube.

In a further, alternative embodiment, it is provided that the brace element has such a degree of flexural strength that, when a tensile force acts on the catheter tube, its alignment changes from the proximal side to the distal side. This means that it is preferably provided that at least one direction component of the longitudinal axis of the brace element is reversed when the specific tensile force comes into effect, namely from the proximal side to the distal side.

Here, the tensile force from which the change of direction of the brace element is effected can be the specific tensile force, wherein in this design, the catheter is preferably not designed in such a manner that a connection between the affixing device and the catheter tube is released when the specific tensile force acts, but that the affixing effect is abandoned as a result of tipping or rolling of the brace element.

The catheter can also be designed in such a manner that the tensile force from which the change of direction of the brace element is effected is lower than the specific tensile force, so that with a lower tensile force than the specific tensile force, a change of direction of the brace element can initially be registered, while, however, the affixing effect is sustained due to the brace element. If the tensile force increases up to the value of the specific tensile force, the release of the affixing device from the catheter tube as described above occurs in the sense that a relative movement between the affixing device and the catheter tube is made possible.

In a further, advantageous design, it is provided that the catheter according to the invention comprises a port system at its proximal end. In the sense of the invention, this port system is a subcutaneously positionable hollow space which is connected to the catheter tube and which is designed to receive active substances such as amino acids and glucose, as well as for the infusion of these active substances through the catheter tube.

BRIEF DESCRIPTION OF THE DRAWINGS

The invention will now be explained with reference to the exemplary embodiments shown in the attached drawings, in which.

DESCRIPTION OF SPECIFIC EMBODIMENTS OF THE INVENTION

Figure 1:
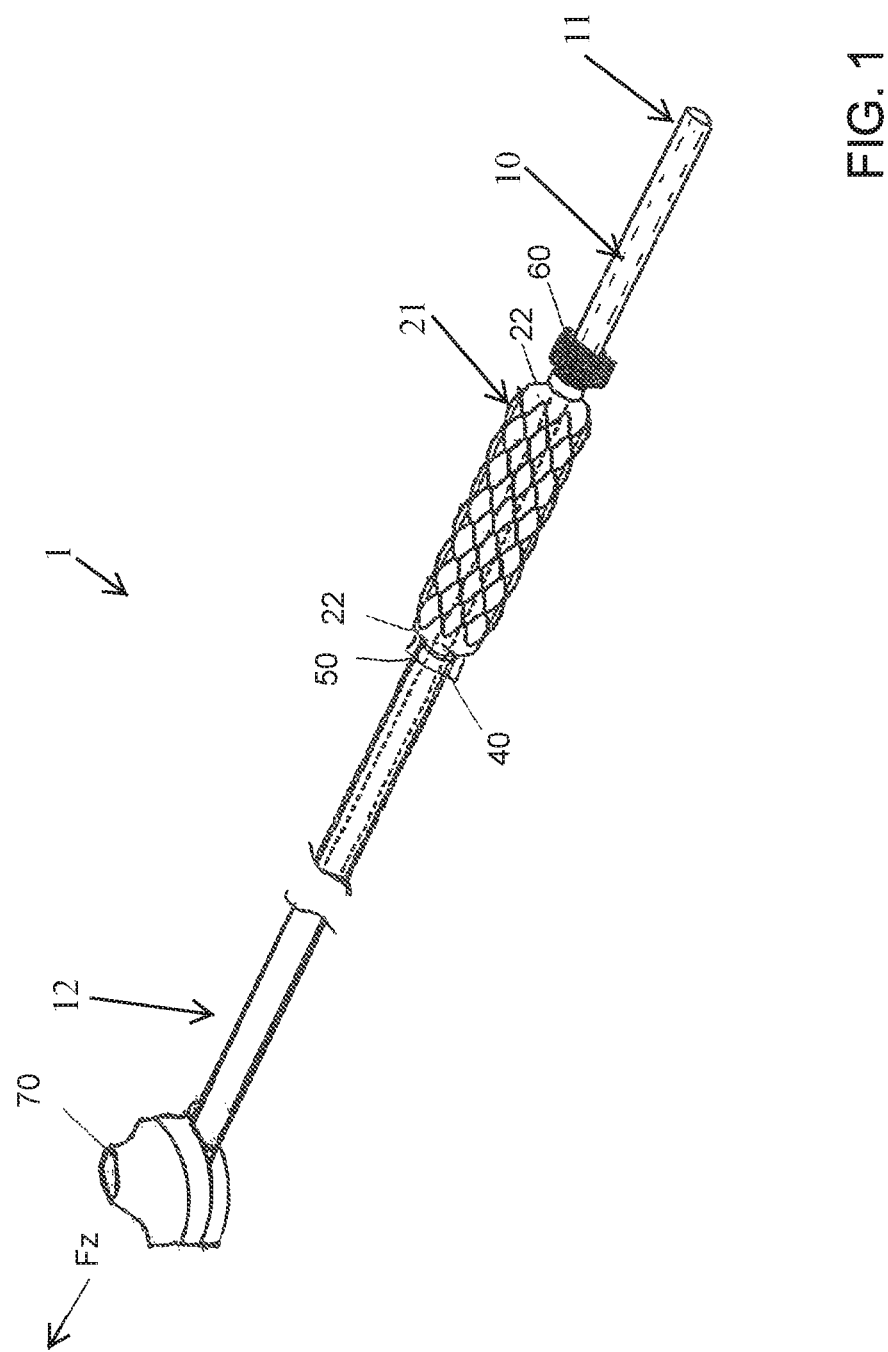
FIG. 1 shows a perspective view of a catheter according to the invention with a stent.

The overall structure of a catheter 1 according to the invention can be seen particularly clearly in FIG. 1. This is a catheter 1 which can be inserted through the abdominal wall and front wall placenta of the mother directly into the umbilical vein of the child while the procedure is monitored using ultrasound. The proximal end 12 of the catheter 1 comprises a port system 70. The port system 70 can be implanted subcutaneously. Through this port system 70, amino acids and glucose can be directly and intravenously infused to the foetus on a continuous basis.

Here, the catheter 1 according to the invention is not shown to scale, but is in general significantly longer than is shown in FIG. 1. The embodiment of the catheter 1 according to the invention shown in FIG. 1 comprises a stent with a hollow cylinder section 21 made of a mesh material, which on both sides comprises a hollow truncated cone or hollow spherical segment 22 with a suitable opening as an aperture for the catheter tube 10. In the direction of the distal end 11 of the catheter tube 10, the catheter 1 comprises a form element 60, the diameter of which is larger than that of the catheter tube 10.

Proximal to the hollow cylinder section 21, a sleeve 50 is arranged which is firmly connected to the hollow cylinder section 21, if necessary via a hollow truncated cone 22 or a hollow spherical segment 22.

A force, form and/or material-fit connection 40 exists between the sleeve 50 and the catheter tube 10, and between the form element 60 and the catheter tube 10.

Here, the catheter 1 is not restricted to the present design with the distal form element 60 and the proximal sleeve 50, but in FIG. 1, the form element 60 and the sleeve 50 are arranged on the catheter tube 10 solely for the purpose of clarifying several different aspects of the invention. In certain design variants of the catheter 1, this can be designed with the form element 60 but without the sleeve 50, or vice-versa with the sleeve 50, but without the form element 60.

During implantation of the catheter 1, a mandarin is pushed in through the proximal end 12 of the catheter 1, so that the friction forces which act on the catheter tube 10 during the insertion of the mandarin expand it and the hollow cylinder section 21 is subjected to a tensile force. Due to this tensile force, the hollow cylinder section 21 extends in length, reducing its diameter. In this form, the catheter 1 and in particular the hollow cylinder section 21 can be optimally positioned in an opening in the tissue. If the mandarin is withdrawn from the proximal end 12 of the catheter 1, the tensile stress is reduced in the catheter tube 10 and thus also in the hollow cylinder section 21, so that the hollow cylinder 21 again contracts, enlarging its diameter. The elastic restoring forces here create pressing forces on the walls of the tissue opening, so that the hollow cylinder section 21 and, as a result of the mechanical connection via the sleeve 50 and/or via the form element 60, the catheter tube 10 is affixed in the tissue. As a result, it is achieved that the distal end 11 essentially remains reliably in the required position, even when the foetus or the mother are moving. Through the port system, nutrients can be dosed and infused through the catheter tube 10.

The catheter 1 can here be designed in such a manner that the force, form and/or material-fit connection 40 between the sleeve 50 and the catheter tube 10 is released when a specific tensile force Fz of e.g. 10 N is applied on the proximal end 12. As a result, the hollow cylinder section 21 remains in the tissue and the catheter tube 10 can be withdrawn from the hollow cylinder section 21. In this design, the arrangement of the form element 60 shown should preferably be avoided.

The sleeve can also be arranged on the distal side of the hollow cylinder section 21, i.e. instead of the form element 60. However, if the catheter 1 is equipped with the form element 60, the hollow cylinder section 21 and/or the hollow truncated cone arranged in a distal position on the hollow cylinder section 21 or a hollow spherical segment 22 arranged there should be designed in such a manner that, when the specific tensile force Fz of e.g. 10 N is applied on the proximal end 12, the respective hollow truncated cone or the respective hollow spherical segment 22 and/or the hollow cylinder section 21 expand in such a manner that the form element 60 can slide through these without causing a relative movement between the form element 60 and the catheter tube 10. In this embodiment, a sleeve 50 should preferably be arranged on the proximal end of the hollow cylinder section 21.

However, the invention is not restricted to designing the catheter 1 either with the form element 60 or with the sleeve 50, but both the sleeve 50 and the form element 60 can be arranged simultaneously on a catheter, and develop their respective effect, whereby in this case, they are to be realised in such a manner that both the sleeve 50 and the form element 60 affix the hollow cylinder section 21 with such forces on the catheter tube that, the affixing is however abandoned when the specific or a greater tensile force Fz acts on the proximal end.

Figure 2:
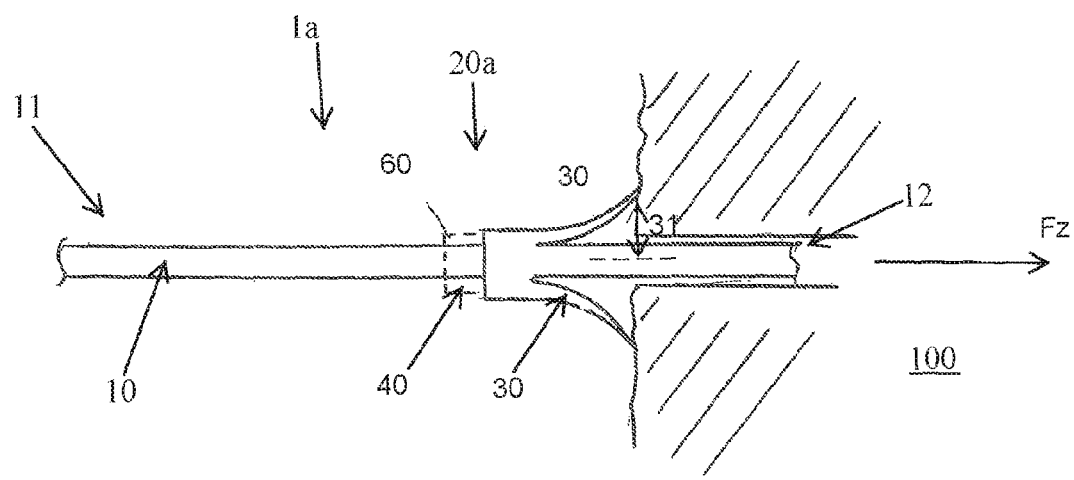
FIG. 2 shows the side view of a section of a catheter according to the invention with two brace elements.
Figure 3:
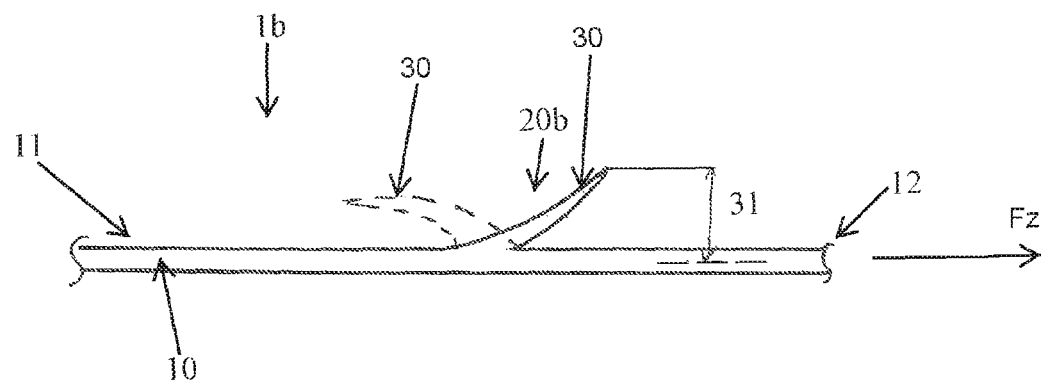
FIG. 3 shows the side view of a section of a catheter according to the invention with one brace element.

FIGS. 2 and 3 show alternative embodiments of the catheter 1a and 1b, respectively, wherein in FIG. 2, the affixing device 20a is realised by 2 brace elements 30 which are connected to the catheter tube 10 by means of a force, material and/or form-fit connection 40. The ends of the brace elements 30 which point in the direction of the proximal end 12 of the catheter tube 10 are at a greater distance 31 from the longitudinal axis of the catheter tube 10 than from its surface. This ensures that the catheter tube 10 is at least prevented from being displaced in the direction of the proximal end 12 when the brace elements 30 are attached to the tissue 100. The brace elements 30 are here preferably made of an elastic material, e.g. a relatively soft synthetic material, so that they can be guided through the opening in the tissue 100 and can expand after having been guided through, enabling them to rest on the tissue 100, as is shown in FIG. 2.

In a similar embodiment to that indicated in FIG. 1, in case of this catheter 1a with brace elements 30, a form element 60 can also be arranged on the distal side of the affixing device 20a, wherein in this case the force, form and/or material-fit connection 40 is preferably created between the form element 60 and the catheter tube 10. This connection 40, which can also be present in the affixing device 20a itself and/or in the form element 60, is designed in such a manner that it is released when the specific tensile force Fz acts on the proximal end 12. This enables the catheter tube 10 to be withdrawn from the affixing device 20a.

Alternatively, the affixing device 20a can be realised in such a manner that it expands when the specific tensile force Fz acts on the proximal end 12, in such a manner that the form element 60, which remains firmly arranged on the catheter tube 10, moves through the affixing device 20a, thus abandoning the affixing effect.

A further alternative design is shown in FIG. 3, in which the affixing device 20b consists of a brace element 30 which can be an integral component of the material of the catheter tube 10. Here, the present invention is not restricted to the number of brace elements shown in FIGS. 2 and 3, but in any of the embodiments shown, a different number of brace elements 30 can be arranged.

The brace element shown in FIG. 3 is designed in such a manner that when the specific tensile force Fz acts on the proximal end 12 of the catheter tube 10, its alignment changes from the proximal end 12 towards the distal end 11, and preferably it becomes tightly attached to the catheter tube 10 in such a manner that the catheter tube can be drawn together with the brace element 30 through an opening in the tissue. In this embodiment, the distance 31 from the tip of the brace element 30 to the longitudinal axis of the catheter tube 10 is also designed in such a manner that a displacement of the catheter tube 10 is prevented as long as the specific tensile force Fz is not applied.

With the shown embodiments of the catheter according to the invention, its catheter tube can be positioned in a simple, reliable, flexible and compatible manner in the placenta or in the cavum uteri.

In order to ensure the removal of the catheter (1, 1*a*) should certain indications occur, e.g. when the waters break prematurely, a mandrin is inserted into the catheter (1, 1*a*), pulling apart the catheter (1, 1*a*) and the affixing device (20, 20*a*).

Here, the affixing device (20, 20*a*) reduces the size of its diameter, so that it can be withdrawn together with the catheter tube 10.

However, if a very rapid removal of the catheter (1, 1*a*) is necessary, or it is not practical to insert the mandrin, the affixing effect of the affixing device (20, 20*a*) can simply be removed by applying the specific tensile force on the proximal end 12, so that the catheter tube 10 is released and can be withdrawn. The affixing device (20, 20*a*) remains in the placenta or in the uterus and is later ejected from the body during the birth together with the placenta and amnions.

The catheter (1, 1*a*, 1*b*) can be used to apply an infusion of amino acids and glucose for the treatment of IUGR.

This enables direct, intravenous intrauterine administration of medication (e.g. Digoxin and Amiodaron in cases of foetal tachycardia) to be ensured.

However, the catheter (1, 1*a*, 1*b*) can also be used for other infusions, e.g. for ongoing amnioinfusion following premature breaking of the waters or for removing fluid from organs or body cavities in humans and animals. The catheter (1, 1*a*, 1*b*) is particularly suitable for intrauterine application for unhealthy foetuses with an infra/supra-vesical obstruction, hydrothorax, cysts, etc.

What is claimed is:

1. A catheter for realising a volume flow into or out of a human or animal organ, comprising a catheter tube and, at a distance from a distal end of the catheter, an affixer that mechanically affixes the catheter in tissue of the human or animal organ, said affixer sized and shaped to fit and attach inside tissue of the organ;
    wherein said catheter tube is selectably releasable and detachable from said affixer when said affixer is positioned in the tissue, whereby the affixer has an aperture therethrough, said aperture sized and shaped for said catheter tube to pass therethrough;
    wherein the catheter is designed in such a manner that the affixer abandons an affixing effect when a specific tensile force of at most 30 N acts on the catheter tube;
    wherein the catheter comprises a distal form element over or on the catheter tube, in relation to a position of the affixer, of which an inner diameter is larger than an outer diameter of the catheter tube, wherein the affixer is designed in such a manner that, due to the specific tensile force acting on the catheter tube, said affixer expands on an edge of said catheter tube facing towards the catheter tube and the form element in such a manner that the catheter tube can be drawn together with the form element through the affixer.

2. The catheter according to claim 1, wherein the catheter is designed in such a manner that the affixer abandons the affixing effect when the specific tensile force of at most 20 N acts on the catheter tube.

3. The catheter according to claim 1, wherein the affixer abandons the affixing effect when the specific tensile force of at most 10 N acts on the catheter tube.

4. The catheter according to claim 1, wherein the affixer is arranged at a distance of one-tenth to one-third of a length of the catheter from a distal end of said catheter.

5. The catheter according to claim 4, wherein the catheter is designed in such a manner that said catheter expands when heat is applied.

6. The catheter according to claim 1, wherein the affixer is embodied by a stent which comprises a hollow cylinder section made of mesh material.

7. The catheter according to claim 6, wherein the stent is designed in such a manner that said stent expands due to elasticity of said stent when a tensile stress acting in a longitudinal axis of the hollow cylinder is reduced.

8. The catheter according to claim 1, wherein the affixer is a brace element which, in profile, is in sections further away from a longitudinal axis of the catheter tube than an outer side of the catheter tube.

9. The catheter according to claim 8, wherein the brace element is elastic, and the catheter tube essentially runs tangentially to the brace element.

10. The catheter according to claim 8, wherein the brace element has such a degree of flexural strength that, when a tensile force acts on the catheter tube, an alignment changes from a proximal side to a distal side.

11. The catheter according to claim 1, wherein the catheter has a force-fit or a form-fit or a material-fit connection between the affixer and the catheter tube, and said force-, form- or material-fit connection is designed in such a manner that said force-, form- or material-fit connection is released when the specific tensile force acts on the catheter tube.

12. The catheter according to claim 1, wherein the catheter comprises a port system on a proximal end of said catheter.

13. The catheter according to claim 1, wherein the catheter tube is elastically deformable and wherein said affixer abandons the affixing effect when the specific tensile force acts on the catheter tube before the tissue is harmed.

14. The catheter according to claim 1, wherein said catheter tube is elastically deformable and wherein said catheter tube is released from said affixer when a tensile force of at least the specific tensile force acts on a proximal end of said catheter tube.

15. The catheter according to claim 14, wherein said specific tensile force is 10 N.

16. The catheter according to claim 14, wherein said catheter tube has a first diameter when no friction force is acting thereon, and wherein said catheter tube has a second diameter larger than said first diameter when a specific friction force acts thereon.

17. The catheter according to claim 1, wherein said affixer is elastically deformable and wherein said affixer is configured to be positioned in the organ when a tensile force of at least the specific tensile force acts on the affixer.

18. The catheter according to claim 17, wherein said affixer has a first diameter when no tensile force is acting thereon, and wherein said affixer has a second diameter smaller than said first diameter when the tensile force of at least the specific tensile force acts thereon.

19. The catheter according to claim 17, wherein said affixer is configured to be implanted in the organ when a tensile force of less than the specific tensile force acts on the affixer.

20. The catheter according to claim 1, wherein said affixer abandons the affixing effect when the specific tensile force of at most 5 N to 10 N acts on the catheter tube.

* * * * *